United States Patent [19]

Leighton

[11] 4,377,958
[45] Mar. 29, 1983

[54] REMOTELY OPERATED MICROTOME

[75] Inventor: Stephen B. Leighton, Maplewood, N.J.

[73] Assignee: The United States of America as represented by the Secretary of the Department of Health and Human Services, Washington, D.C.

[21] Appl. No.: 250,269

[22] Filed: Apr. 2, 1981

[51] Int. Cl.³ .............................................. G01N 1/06
[52] U.S. Cl. .................................. 83/411 R; 83/412; 83/582; 83/589; 83/915.5
[58] Field of Search .................... 83/410, 411 R, 414, 83/582, 589, 915.5, 409, 412

[56] References Cited

U.S. PATENT DOCUMENTS

| 790,564 | 5/1905 | Dunn | 83/411 R |
|---|---|---|---|
| 2,843,014 | 7/1958 | Sitte . | |
| 3,191,477 | 6/1965 | Danon . | |
| 3,293,972 | 12/1966 | Burkhardt et al. . | |
| 3,462,969 | 8/1969 | Grasenick et al. | 83/915.5 X |
| 3,603,189 | 9/1971 | Stachl | 83/915.5 X |
| 3,613,492 | 10/1971 | Soderkvist . | |
| 3,688,500 | 9/1972 | Chancel . | |
| 3,691,889 | 9/1972 | Forsstrom . | |
| 3,845,659 | 11/1974 | Wikefeldt . | |

Primary Examiner—James M. Meister
Attorney, Agent, or Firm—Browdy and Neimark

[57] ABSTRACT

A miniature microtome assembly with a bellows-operated blade on an arm swingably mounted on a flexible hinge. The specimen is secured in a chuck on a support arm pivoted on a flexible hinge. The specimen is fed toward the cutting path of the blade by a suitably supported feed screw operatively driven by a nut gear actuated by a bellows for coarse advancement steps, and has a fine advance provided by a piezoelectric crystal mounted between the specimen stage and the top end of the feed screw, thereby providing coarse and fine feed of the specimen. The assembly may be contained in a vacuum chamber and the active parts are operated by remote control.

12 Claims, 7 Drawing Figures

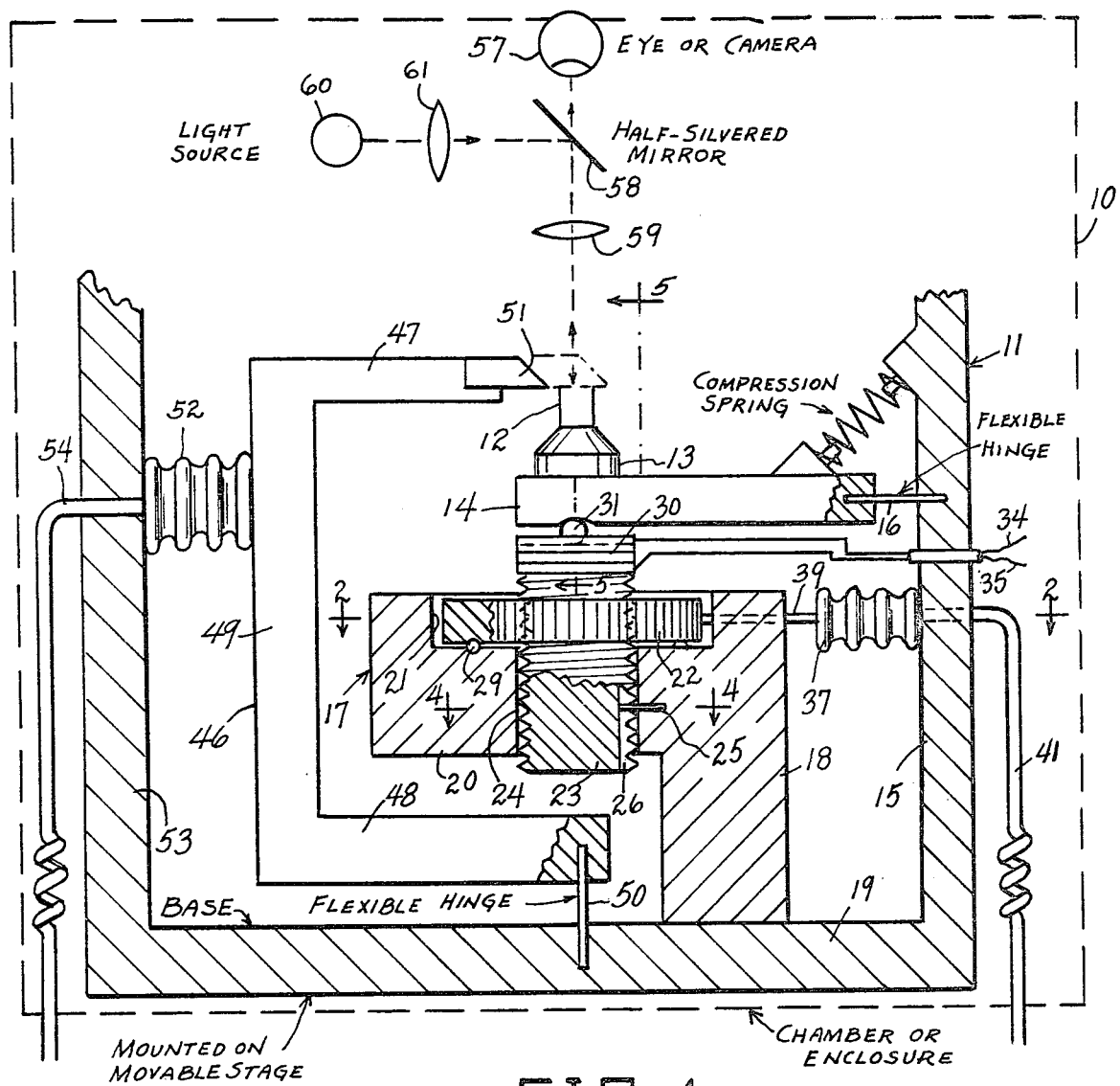
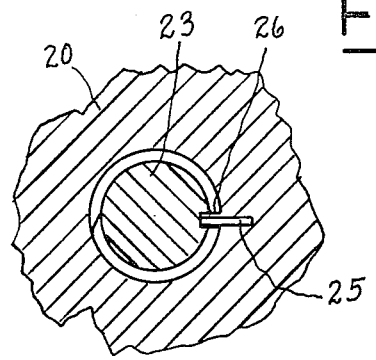
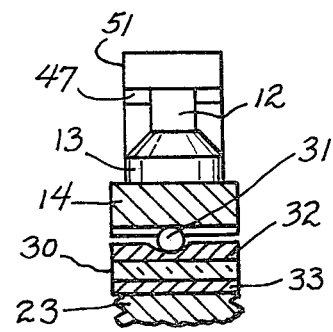
FIG.1
FIG.4
FIG.5

REMOTELY OPERATED MICROTOME

FIELD OF THE INVENTION

This invention relates to microtomes, and more particularly to a remotely controlled microtome assembly constructed and arranged to remove thin sections from a block of tissue while said block is supported within a vacuum chamber or similar enclosure associated with an optical microscope or a scanning electron microscope, so as to allow exact observation of otherwise hidden tissue structure.

BACKGROUND OF THE INVENTION

Existing microtomes are relatively large and bulky, employ thermal expansion means or mechanical means for advancing the specimen, and use components which are not compatible with operation within the vacuum chamber of an optical microscope or of a scanning electron microscope. Thus, in the standard microtome there is no satisfactory provision for precise remote control of the cutting position of the specimen, and the advancement of the specimen for slicing cannot be controlled with the precision required to obtain exact observation of the tissue structures revealed in very small successive cutting steps. Therefore, there is a definite need for a relatively compact, accurately controllable microtome structure compatible with such operation within the vacuum chamber, or similar enclosure, associated with an optical microscope or a scanning electron microscope.

A preliminary search of the prior art revealed the following prior U.S. patents substantially showing the present state of the art:
Sitte, U.S. Pat. No. 2,843,014,
Darron, U.S. Pat. No. 3,191,477,
Burkhardt et al, U.S. Pat. No. 3,293,972,
Soderqvist, U.S. Pat. No. 3,613,492,
Chancel, U.S. Pat. No. 3,688,500,
Forsstrom, U.S. Pat. No. 3,691,889,
Wikefeldt, U.S. Pat. No. 3,845,659.

SUMMARY OF THE INVENTION

The microtome assembly of the present invention is relatively compact, employs piezoelectric advance for fine adjustment of the cutting position of the specimen, is provided with remotely controlled actuating means, and employs flexible hinges, thereby eliminating the need for lubrication. Also, the specimen in its adjusted position is stationary, and the cutting blade is moved, which is the reverse of the arrangement employed in most standard microtomes, and which is more compatible with the precise positioning of images as required for a scanning electron microscope.

In the microtome assembly of the present invention, the knife arm pivots on a flexible hinge, for minimum backlash, and is actuated by a bellows for remote-controlled, smooth operation in a small space with no thermal transients, in comparison to conditions obtained by the use of motors, solenoids, and the like. The specimen is held in a chuck mounted on a flexibly-hinged support arm and is advanced coarsely by a lead screw actuated for forward and rear movement by respective bellows having pawl elements engageable with the teeth of a rotatably-supported gear-shaped drive nut threaddily engaged with the lead screw. Fine adjustment of the specimen is provided by the employment of a piezoelectric crystal enabling fine continuous positional control of the specimen with no thermal effects. The assembly is contained in an enclosure, such as a vacuum chamber, and the active parts are operated by remote control.

Accordingly, a main object of the invention is to provide an improved microtome assembly for use with an optical microscope or with a scanning electron microscope, which overcomes the deficiencies and disadvantages of the previously known microtome devices.

A further object of the invention is to provide an improved microtome assembly which is compatible with operation within the vacuum chamber, or similar enclosure, associated with a microscope and which does not employ thermal expansion means or mechanical direct drive means for advancing the specimen to its cutting position.

A still further object of the invention is to provide an improved microtome assembly which utilizes remote control means for operating its moving parts, whereby it may be effectively employed in the vacuum chamber of an electron microscope or in any other analogous instrument having a relatively non-accessible working space.

A still further object of the invention is to provide an improved microtome assembly which is provided with remotely controlled means for operating its moving parts and is compatible for use within the vacuum chamber of an X-ray microprobe or of a scanning electron microscope, and which has piezoelectric means for precisely adjusting the cutting position of a specimen.

A still further object of the invention is to provide an improved microtome assembly for use with an optical microscope or an electron microscope, and which employs flexible hinges, thereby requiring no lubricant and thus preventing contamination of the space containing the assembly.

A still further object of the invention is to provide an improved microtome assembly operable in the vacuum chamber of an X-ray microprobe or of a scanning electron microscope, which has precision remotely-controlled means for adjusting the cutting position of a specimen and enabling exact observation of tissue structures by allowing very small successive advancement steps for slicing the specimen under study, and being free of thermal effects.

A still further object of the invention is to provide an improved miniature microtome assembly which is very compact in size, which is compatible for use in the vacuum chamber of an X-ray microprobe or of a scanning electron microscope, which has an arrangement for very precise fine adjustments of the cutting position of a specimen, said arrangement including a piezoelectric crystal supporting the specimen and being electrically actuated for adjusting the position of the specimen, and having coarse position-adjustment means actuated by remotely-controlled fluid-operated, specimen-advancing flexible bellows, and being further provided with a flexibly-hinged knife arm carrying a cutting blade, the hinged knife arm being also actuated by a remotely-controlled flexible bellows.

A still further object of the invention is to provide an improved microtome device which operates to remove thin sections from a block of tissue while said block is held in a fixed adjusted position within the vacuum chamber of an optical microscope or of a scanning electron microscope, to allow exact observation of otherwise hidden three-dimensional structure, the thin sections being removed by the swinging action of a hinged knife assembly relative to the fixed block, fine adjustment of the advance of the block being obtained by means of the action of a piezoelectric crystal on which the block is supported.

BRIEF DESCRIPTION OF THE DRAWINGS

Further objects and advantages of the invention will become apparent from the following description and claims, and from the accompanying drawings, wherein:

FIG. 1 is a vertical cross-sectional view taken through a portion of an optical microscope system provided with an improved microtome assembly constructed in accordance with the present invention.

FIG. 4 is a fragmentary horizontal cross-sectional view taken substantially on line 4—4 of FIG. 1.

FIG. 5 is a fragmentary vertical cross-sectional view taken substantially on line 5—5 of FIG. 1.

DETAILED DESCRIPTION OF PREFERRED EMBODIMENTS

Figure 2:
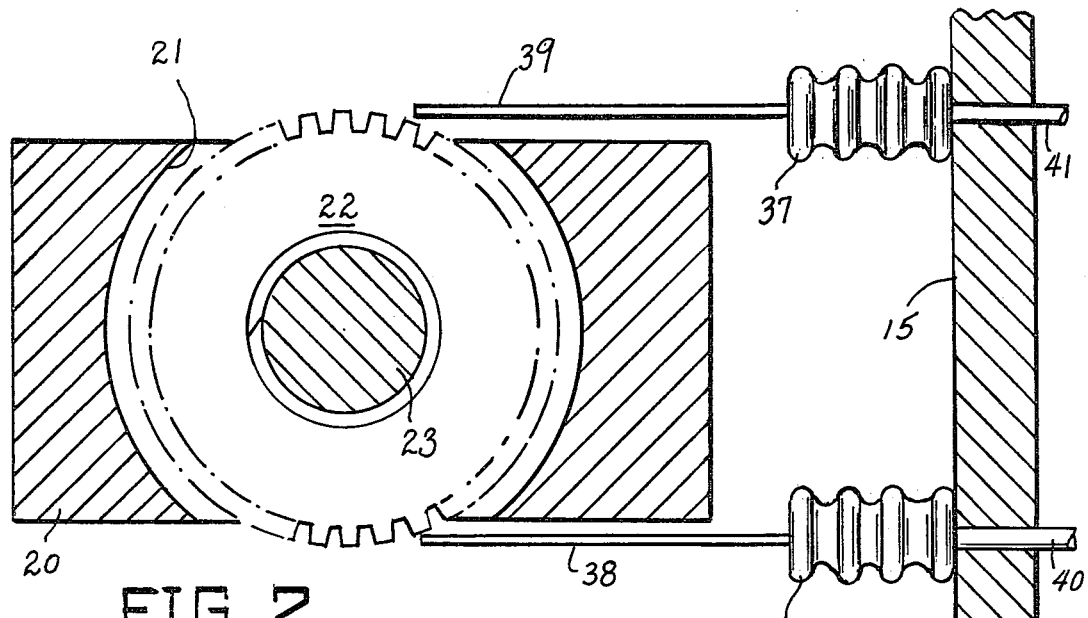
FIG. 2 is an enlarged horizontal cross-sectional view taken substantially on line 2—2 of FIG. 1.

Referring to the drawings, and more particularly to FIGS. 1 to 5, there is shown an enclosure 10 in which a tissue specimen is to be held for cutting thin sctions therefrom and for examination of the resultant freshly exposed surface thereof to enable observation of otherwise hidden 3-dimensional tissue structure. In FIG. 1, the observation is made via a substantially conventional optical microscope system, as will be presently described.

In the arrangement shown in FIG. 1, the tissue specimen, in the form of a substantially rigid block 12, is mounted in a chuck 13 which is rigidly secured on an elongated, downwardly biased, support arm 14 which is connected to a vertical wall 15 of a base 11 by a resilient horizontal leaf spring 16 forming a flexible hinge. Designated generally at 17 is a sample-positioning assembly comprising an upstanding main bracket 18 rigidly secured to the bottom wall 19 of the base 11 and having a horizontal top arm 20 underlying the support arm 14. Top arm 20 has a recess 21 in which is rotatably mounted a gear nut 22 which is axially aligned with chuck 13. A vertical travelling screw 23 is threadedly engaged with the gear nut 22 and is slidably received in a vertical bore 24 provided in horizontal arm 20. Screw 23 is held against rotation by a guide pin 25 rigidly secured in arm 20 and extending slidably into a vertical keyway 26 provided in screw 23.

Suitable ball bearings 29 may be employed to allow smooth rotation of the gear nut 22 in recess 21.

A piezoelectric crystal assembly 30 is mounted on the top end of screw 23, and a bearing ball 31 is provided between arm 14 and crystal assembly 30, the bottom surface of arm 14 and the top electrode 32 of crystal assembly 30 being suitably cylindrically recessed to cooperatively and retentively receive the top and bottom portions of bearing ball 31, as shown in FIGS. 1 and 5.

Coarse vertical positioning of the tissue specimen block 12 is provided by rotating the gear nut 22. Fine vertical positioning adjustments of the tissue specimen are provided by applying suitable d.c. voltages across the top and bottom electrodes 32, 33 of the piezoelectric crystal assembly 30 via connection wires 34, 35, extending outside the chamber 11.

As shown in FIG. 2, the teeth of gear nut 22 project beyond the opposite sides of horizontal arm 20. Respective resilient gear-actuating bellows 36, 37 are secured to base wall 15, directed substantially tangentially relative to the gear nut 22. Bellows 36 is provided with a resilient axial pawl rod 38 drivingly engageable with the gear teeth responsive to expansion of bellows 36 so as to rotate gear nut 22 clockwise, as viewed in FIG. 2, and to thereby elevate screw 23. Similarly, bellows 37 is provided with a resilient axial pawl rod 39 drivingly engageable with the gear teeth responsive to expansion of bellows 37 so as to rotate gear nut 22 counterclockwise, as viewed in FIG. 2, and to thereby lower screw 23. Bellows 36 and 37 are connected via conduits 40, 41 and 3-way valves 42, 43 to respective manually operated air cylinders 44, 45 for selectively actuating said bellows from outside the chamber 10.

Designated generally at 46 is a substantially C-shaped member having horizontal top and bottom arms 47 and 48 and a long vertical main arm 49. The end portion of bottom arm 48 is hingedly connected by a leaf spring hinge member 50 to the base bottom wall 19, located substantially in vertical alignment with chuck 13. Secured to the end of horizontal top arm 47 is a cutting blade 51 which normally extends adjacent to the tissue specimen block 12. A blade-actuating resilient bellows 52 is secured between the vertical wall 53 of base 11 and the vertical main arm 49 of the blade-supporting member 46. Expansion of bellows 52 rotates member 46 clockwise, as viewed in FIG. 1, and swings blade 51 substantially horizontally through a cutting stroke. Bellows 52 is connected via a conduit 54 to a manually operated external hydraulic cylinder 55, employing a suitable hydraulic fluid, such as ethanol. Thus, force applied to the piston 56 of said cylinder is transmitted via the hydraulic fluid to the bellows 52, causing expansion thereof and causing the blade 51 to perform a cutting stroke. Upon release of the actuating force, the blade 51 is retracted by the restoring actions of the flexible leaf spring hinge 50 and the resilient bellows 52.

It will be seen that the knife arm assembly 46 pivots on the flexible hinge 50 with minimum backlash and is controlled for remote, smooth operation in the relatively limited space within the base 11, with no thermal transients such as are present where motors, solenoids, or the like, are employed. Coarse advance of the specimen block 12 is obtained by actuation of the gear nut 22, and fine continuous adjustment of the specimen position can be provided by the piezoelectric crystal assembly 30, as above described, again with no thermal effects and with precise remotely controlled operation.

Exact observation of the surfaces exposed by the removal of thin sections of the specimen block 12 may be provided by the typical optical system shown diagrammatically in FIG. 1. This typical system comprises an eyepiece or camera 57 vertically aligned with the specimen block, with an interposed 45° half-silvered mirrow 58 and focussing lens 59. The specimen surface is illuminated by a light source 60 via a lens 61, the bottom reflecting surface of the 45° mirror 58 and lens 59. The light reflected from the specimen surface travels upwardly to the eyepiece or camera 57 through the lens 59 and the half-silvered mirror 58.

Figure 6:
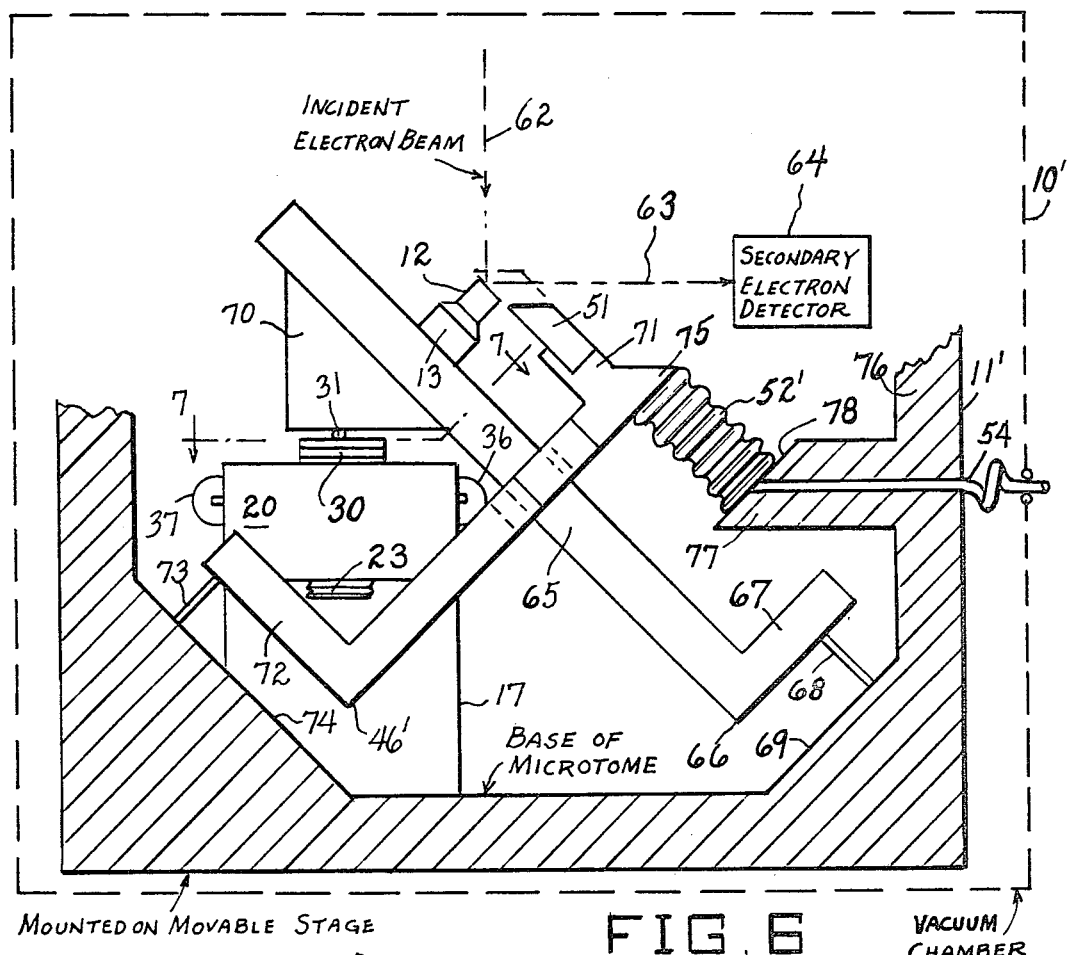
FIG. 6 is a vertical cross-sectional view taken through a portion of the vacuum chamber of a scanning electron microscope provided with another form of improved microtome assembly constructed in accordance with the present invention.
Figure 7:
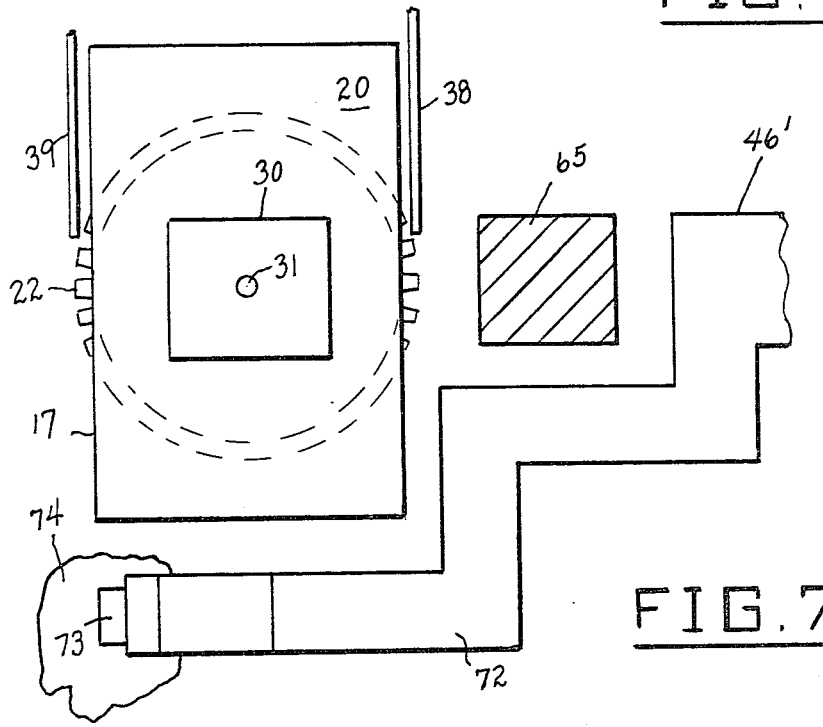
FIG. 7 is a fragmentary enlarged cross-sectional view taken substantially on line 7—7 of FIG. 6.

Referring to FIGS. 6 and 7, 10' designates the vacuum chamber of a scanning electron microscope provided with another form of microtome assembly according to the present invention, wherein the incident electron beam, indicated at 62, strikes the cut surface of the specimen block 12 at a 45° angle, and the secondary electrons emitted from the specimen surface leave said surface and define a beam 63 which impinges on a secondary electron detector 64. In this embodiment, the chuck 13 is mounted on the longer main element 65 of a generally L-shaped member 66, the shorter foot element 67 thereof being connected by a flexible leaf spring 68, acting as a flexible hinge, to a 45°-inclined bottom corner portion 69 of the base 11'. The leaf spring hinge member 68 is contained in a 45°-inclined plane substantially aligned with the specimen block 12, so that the block 12 is movable substantially perpendicular to said plane responsive to pivoting of the relatively long support arm 66 around the effective hinge axis of the flexible hinge 68. Movement of the support arm 66 to adjust the position of the tissue specimen 12 for cutting is achieved by means of a specimen-positioning assembly 17 similar to that employed in the first-described embodiment, the bearing ball 31 of said assembly being engaged between the piezoelectric crystal assembly 30 and a triangular block 70 rigidly secured to the underside of arm element 65. The structure and mode of operation of the sample-positioning assembly 17 are similar to that previously described in connection with the embodiment of FIGS. 1 to 5.

A blade-supporting member 46' has a top arm 71 to which the cutting blade 51 is rigidly secured and has a parallel bottom arm 72 connected by a leaf spring flexible hinge 73 to a 45°-inclined opposite bottom corner portion 74 of base 11'. Leaf spring 73 is substantially coplanar with the axis of chuck 13, although bottom arm 72 is offset laterally relative to top arm 71 to provide clearance for the specimen-positioning assembly 17, as shown in FIG. 7. Top arm 71 is substantially in the same vertical plane as the specimen block 12, so that rotation of member 46' in a counterclockwise direction around the hinge axis defined by flexible hinge spring 73, as viewed in FIG. 6, moves the cutting blade 51 through a cutting stroke.

Top arm 71 is provided with a triangular corner abutment lug 75, and the vertical wall 76 of base 11' has an inwardly projecting abutment lug with a 45°-inclined end surface, shown respectively at 77 and 78, the end surface 78 opposing the lug 75. A resilient bellows 52' is connected between lug 75 and lug surface 78, said bellows being connected via a conduit 54 to a hydraulic operating cylinder corresponding to hydraulic cylinder 55 in the first-described embodiment of the invention. When force is applied to the piston of the hydraulic operating cylinder, bellows 52' is expanded and drives blade 51 through a cutting stroke. The blade 51 is retracted responsive to release of the force, as in the previously described embodiment shown in FIGS. 1 to 5.

As shown in FIG. 6, the 45°-inclined leaf spring 73 and bellows 52' normally support the main portion of member 46' in a 45°-inclined plane substantially perpendicular to the opposite 45°-inclined arm element 65. The cutting position of the specimen block 12 can be coarsely adjusted in the same manner as previously described, by rotating the gear nut 22, and fine adjustment of the specimen block can be accomplished by means of the piezoelectric crystal assembly 30. The flexible hinges 68 and 73 respectively permit adjustment of the specimen block and movement of cutting blade 51 through a cutting stoke, substantially without backlash and without thermal effects, as well as enabling precise remote control from outside the vacuum chamber.

Figure 3:
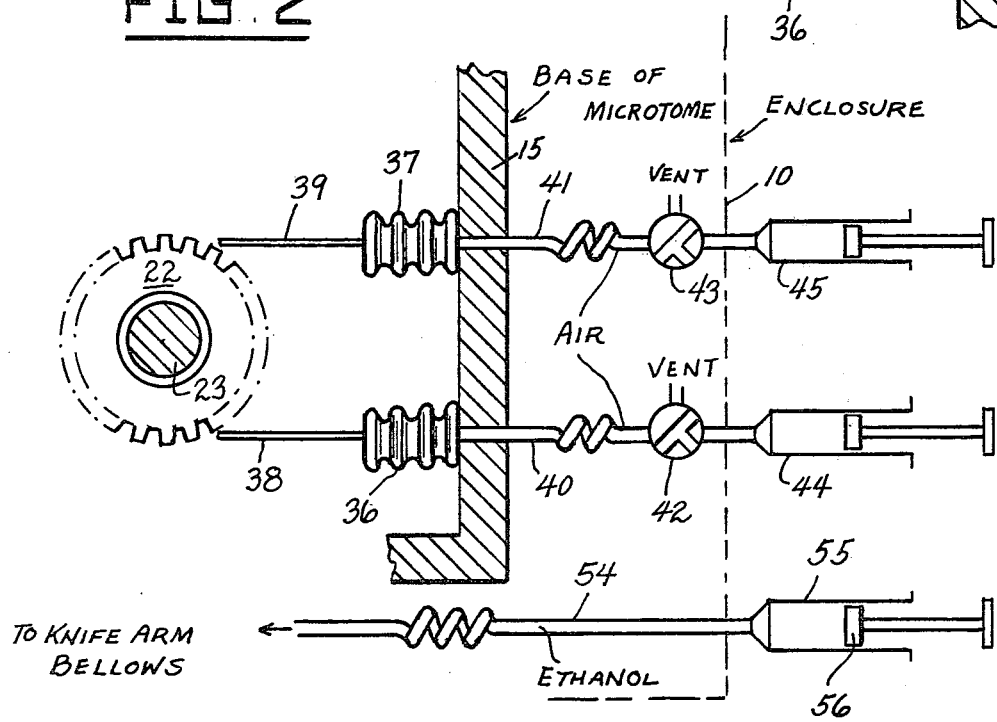
FIG. 3 is a diagrammatic, reduced-scale horizontal cross-sectional view showing the bellows-operating system employed in the microtome assembly of FIG. 1.

Referring to FIG. 3, it can be seen that normally the resilient bellows 36, 37 maintain their pawl rods 38, 39 in retracted positions, so that when one of said bellows is actuated, the rod association with the other bellows will not interfere with rotation of the gear nut 22. Therefore, one of the pawl rods is held retracted, out of the way of the gear teeth, while the other is employed to push the gear around, one tooth at a time, retracting after pushing each tooth.

Furthermore, by employing suitable pawl configurations, vacuum may be employed to rotate the gear nut 22, by means of the bellows 36, 37, instead of employing positive air pressure.

Also, within the spirit of the present invention, manually operated cylinders 44, 45 may be replaced by computer-controlled solenoid valves connecting their associated bellows to a fluid pressure source or vacuum, and hydraulic cylinder 55 may be operated by motor drive means instead of by hand. The cylinder 55 may contain ethanol or any suitable low-viscosity imcompressible liquid. Thus, the motion of piston 56 is directly related to knife motion.

The piezoelectric crystal assembly 30 is driven from any suitable external electrical power supply, for example, from an external 1000 volt d.c. supply source.

While certain specific embodiments of an improved remotely operated microtome device have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A microtome assembly comprising a base, first support arm means, means to hingedly mount said first support arm means on said base, specimen-holding means on said first support arm means, specimen-advancing means mounted on said base and drivingly engaging said specimen-holding means, second support arm means, means to hingedly mount said second support arm means on said base, cutting blade means, means to mount said cutting blade means on said second support arm means adjacent to and movable with respect to said specimen-holding means for cutting a specimen responsive to motion of said second support arm means on its hingedly mounting means, an enclosure, and said microtome being adapted to be housed within and to operate within said enclosure, means to actuate said specimen-advancing means remotely from outside said enclosure, and means to actuate said second support arm means to drive said cutting blade means in a cutting stroke with respect to a specimen mounted in said specimen-holding means remotely from outside said enclosure.

2. The microtome assembly of claim 1, and wherein the first and second support arm means are hingedly mounted by resilient means connecting the respective support arm means to the base.

3. The microtome assembly of claim 2, and wherein said resilient means comprises respective leaf springs.

4. The microtome assembly of claim 1, and wherein the means to actuate the specimen-advancing means includes piezoelectric crystal means interposed between said first support arm means and the base.

5. The microtome assembly of claim 1, and wherein said specimen-advancing means includes screw means operatively supporting said piezoelectric crystal means, drive nut means threadedly engaged with said screw means and rotatably mounted on the base, and externally-actuated means to rotate said drive nut means.

6. The microtome assembly of claim 5, and wherein the means to rotate said drive nut means comprises flexible bellows means mounted on the base and having pawl means drivingly engageable with said drive nut means responsive to distortion of said bellows means, and said remote actuating means comprises external fluid pressure means communicatively and operatively connected to said flexible bellows means.

7. The microtome assembly of claim 6, and wherein said drive nut means comprises a toothed gear, and wherein said pawl means is drivingly engageable with a tooth of said gear responsive to distortion of said bellows means.

8. The microtome assembly of claim 1, and wherein the remote actuating means to rotate said second support arm means comprises flexible bellows means connected between the enclosure and said second support arm means, and external fluid pressure means communicatively and operatively connected to said flexible bellows means.

9. The microtome assembly of claim 1, and wherein said specimen-advancing means comprises coarse advancement screw means drivingly engaging beneath said first support arm means, drive nut means rotatably mounted on the base and threadedly engaged with said screw means, bellows means mounted in the enclosure and having pawl means drivingly engageable with said drive nut means, and external fluid pressure means communicatively and operatively connected to said bellows means.

10. The microtome assembly of claim 9, and wherein said drive nut means comprises a toothed gear and said pawl means comprises a rod element on said bellows means extending substantially tangentially toward said gear and being drivingly engageable with a tooth of the gear responsive to expansion of said bellows means.

11. The microtome assembly of claim 9, and wherein said specimen-advancing means includes specimen fine advancement means comprising piezoelectric crystal means interposed between said screw means and said first support arm means, and means to connect an external operating voltage to said piezoelectric crystal means.

12. The microtome assembly of claim 11, and wherein the first and second support arm means are hingedly connected to the base by resilient leaf springs defining respective flexible hinges yieldably permitting rotation of the support arm means on the base.

* * * * *